United States Patent [19]

Choyce

[11] 4,414,694

[45] Nov. 15, 1983

[54] INTRA-OCULAR LENSES

[76] Inventor: David P. Choyce, 9 Drake Rd., Westcliff on Sea, England

[21] Appl. No.: 435,106

[22] Filed: Oct. 18, 1982

Related U.S. Application Data

[63] Continuation-in-part of Ser. No. 287,628, Jul. 28, 1981, abandoned.

[30] Foreign Application Priority Data

Aug. 5, 1980 [GB] United Kingdom ............... 8025426
May 11, 1981 [GB] United Kingdom ............... 8114325

[51] Int. Cl.$^3$ .............................................. A61F 1/16
[52] U.S. Cl. ...................................................... 3/13
[58] Field of Search ..................... 3/13, 1; 351/160 R, 351/160 H

[56] References Cited

U.S. PATENT DOCUMENTS

| 2,714,721 | 8/1955 | Stone | 3/1 |
| 2,779,751 | 1/1957 | Bredereck et al. | 3/1 X |
| 3,228,741 | 1/1966 | Becker | 3/13 X |
| 4,080,709 | 3/1978 | Poler | 3/13 |
| 4,164,794 | 8/1979 | Spector et al. | 3/1 X |

OTHER PUBLICATIONS

"The Choyce Mark VIII and Mark IX Anterior Chamber Implants" by D. P. Choyce, AM Intra-Ocular Implant Soc. J–vol. V., Jul. 1979, pp. 217–221.

Primary Examiner—Ronald L. Frinks
Attorney, Agent, or Firm—Lewis Messulam

[57] ABSTRACT

An intra-ocular lens which is formed entirely of a polysulfone plastics material. This material is capable of being worked to produce a lens of optical quality, has a refractive index in excess of 1.55 and is capable of being autoclaved in steam at a temperature in excess of 110° C.

3 Claims, 2 Drawing Figures

INTRA-OCULAR LENSES

The present application is a continuation in part of my application, Ser. No. 287,628, filed on July 28, 1981, now abandoned.

The invention relates to intra-ocular lenses, this term being used to include anterior chamber, posterior chamber and pupillary implants.

When an eye develops a cataract, it is necessary to remove the natural lens in order to restore vision. In the absence of any form of lens in the eye, this condition being termed aphakia, it is necessary to wear spectacles of high power and such spectacles are not only inconvenient and unattractive, but they also severely restrict the field of view of the user.

For this reason, various types of implant have been proposed in the past to place an artificial lens at or near the location of the natural lens, allowing the lens to follow movements of the eye. If the lens is selected so as to focus at infinity then it is only necessary to use spectacles at reading distances.

Such implants have been successfully used in the past and the known implants are classified in accordance with the position they adopt in the eye. Pupillary implants, such as iris clip implants, are not generally favoured because of dislocation, damage to the corneal endothelium and pupil blockage which they entail, but both anterior and posterior chamber implants are now being used extensively and successfully.

The present application will be described with particular reference to anterior chamber implants but it is stressed that the improvement of the invention is equally applicable to other forms of intra-ocular lens.

Anterior chamber implants were at one point made exclusively of glass, in particular by pioneers in this field such as Strampelli, Baron and Dannheim, who had appreciated the advantages of being able to sterilise the implant by autoclaving. Dannheim, in particular, persevered and inserted approximately thirty six autoclavable implants, the last being in 1958. The work on anterior chamber implants capable of being autoclaved and which were primarily made of glass was, however, abandoned because of their weight and also because on one or two occasions fractures and later complications occurred, the complications being uveitis, glaucoma and hyphema, which are problems familiar in the present day context in association with injection moulded polymethylmethacrylate (PMMA) anterior chamber implants.

The present day PMMA implants, notably the implants invented by me and sold under the trade designation Choyce Mark VIII and Choyce Mark IX, do enjoy a considerable success but they nevertheless suffer from the disadvantage of being difficult to sterilise.

The choice of size of anterior chamber implant remains and will continue to remain a difficult problem to resolve pre-operatively. Only in the operating room can one be absolutely certain as to the length for the particular recipient's eye. This means that even a skilled operator, every so often, selects an implant which is either too short or too long. The choice of an incorrect implant involves wastage because although implants may be returned to the manufacturer, it is normally found that they cannot be brought back to the necessary high quality finish to justify their being resterilised and shipped back to the operating surgeon.

The best method of sterilisation of PMMA implants is the subject of controversy. The caustic soda method is still used by a major manufacturer in the United Kingdom and when correctly carried out has proved to be perfectly satisfactory. However, this method has come under informed criticism from professional micro-biologists and other scientists connected with the F.D.A. in the United States and the Department of Health and Social Security in the United Kingdom. Thus, this method is still on probation and is not unconditionally accepted.

The other method which is widely practiced is the use of ethylene oxide (ETO). There are numerous reports of sterile hypopyons following the use of anterior chamber implants sterilised with ETO (the toxic lens syndrome). Implants sterilised in this manner can be used satisfactorily if thoroughly washed in normal saline solution before implantation. However, even with this precaution taken, it has been found in practice that the central endothelial cell count in patients may be lower than when the wet sterilisation method is employed.

In particular, with wet sterilisation, the endothelial cell count suffered a loss of 31% in Mark VIII implants before 1975, the loss having been reduced to 23% for current Mark VIII implants and only 17% for current Mark IX implants. This is to be contrasted with Perspex CQ (registered trade mark) implants sterilised in ETO which, in the present day, cause a loss of 34% of the endothelial cell count and, worst of all, injection moulded anterior chamber implants sterilised in ETO where the loss is as high as 47%. The reason for the relatively high loss in endothelial cell count in the Mark VIII implants used for 1975 is that the anterior chamber was not routinely re-inflated with air before the introduction of the implant, thus more endothelial cells were damaged at the time of surgery.

It seems clear from the foregoing that no method of sterilisation of nonautoclavable implants has yet proved totally satisfactory.

As a result of all these difficulties in the manufacture and sterilisation, the cost of implants has been beyond the means of all but the richest industrial nations. Thus, despite the advantages of pseudophakic surgery, poorer countries, who are not lacking in skilled eye surgeons, have not been able to benefit from the technique.

Appreciating the need for an autoclavable implant, I have previously proposed in U.S. Pat. No. 4,315,337 a modified form of the Choyce Mk IX implant made from a hybrid construction, in which the optic of the implant is made of glass and the haptic is made from another material which, like glass, is autoclavable but which can withstand the mechanical stresses. I found, however, that apart from the difficulties in manufacturing the implant, the basic design of the implant caused problems because of its weight.

The object of the present invention is therefore to provide an intra-ocular implant which is capable of being sterilised by autoclaving and which is capable of being stably retained within the eye.

In accordance with the present invention, there is provided an intra-ocular lens which is formed entirely of a polysulfone plastics material which is capable of being worked to produce a lens of optical quality, which has a specific gravity in excess of 1.55 and which is capable of being autoclaved in steam at a temperature in excess of 110° C.

Preferably, the polysulfone material is an aromatic polysulfone containing repeating units having the formula:

[Ar-SO$_2$]

where Ar is a divalent aromatic radical containing at least one unit having the structure:

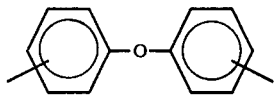

The material which has been successfully used in practice is Udel (registered trade mark) commercially available from the Union Carbide Corporation. This material is composed of repeating units having the structure shown below:

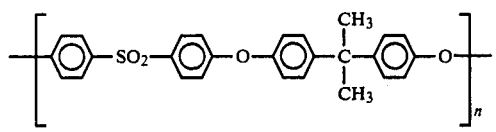

where n = 10 to 500

The selection of a material for use in intra-ocular implantation involves satisfying several important criteria. Of course, a very important factor is that the material should be capable of producing lenses of optical quality. No material can be considered if its optical properties are inferior in quality to those of PMMA since one would be trading off vision against cost. This criterion alone rules out the use of several plastics materials, for example those which are naturally opaque, those which are clouded when autoclaved, those in which cavitation is unavoidable due for example to production of steam within the plastics material and those where stress lines cause striations and variation in refractive index.

The weight of the material in the fluid of the eye, in the case of anterior chamber implants this being the weight in aqueous humor, must be as close as possible to zero to prevent the implant from being dislodged in the event of shock. This requirement places limitations on the acceptable density of the plastics material and favours materials having a higher refractive index since thinner and lighter lenses can then be used to achieve the same level of correction.

It has been found after extensive research that Udel is capable of meeting all these criteria and offers still further the advantage of being permeable by the fluids naturally circulating in the eye.

The material itself is known and its use has in the past been suggested for prosthetic devices. In particular, U.S. Pat. No. 4,164,794 (Spector et al) describes prosthetic devices such as orthopedic and dental prostheses made of Udel, the material being selected for its mechanical properties which are, in fact, excellent. The above patent, however, makes mention only of the properties of relevance to those applications, such as biocompatability and mechanical strength and makes no mention of density, refractive index, optical properties or porosity. The patent thus provides no useful teaching with regard to the use of the same plastics material in intra-ocular implants.

It should be mentioned that the mechanical properties of polysulphone plastics materials do lend themselves to anterior chamber implants of the Choyce Mark IX design where they enable the dimensions of the haptic to be kept down to a bare minimum but, for the reasons given above, one would not select a material because of its mechanical properties alone, there being other more important conditions which must first be met.

U.S. Pat. No. 2,779,751 mentions the use of sulfone-containing plastics materials in prostheses and mentions artificial eyes. The latter patent, while mentioning the optical clarity of such materials, does not in fact suggest polysulfone materials which are capable of being used in intra-ocular surgery. In particular, the plastics materials proposed in that patent and which form the subject of the claims, involve the use of a polymerisation accelerator which comprises a heavy metal or a heavy metal salt amongst which are mentioned iron and copper. The presence of any such material in a plastic would preclude its use for insertion within the eye. Furthermore, the patent does not provide any teaching which would be of assistance in meeting the primary object of the invention, which is to provide an autoclavable implant since the temperature properties are not mentioned.

Consequently, although the material for the manufacture of an autoclavable implant has been in existence for some time, its use in intra-ocular lens implants has not been discovered hitherto and this is despite the fact that the sterilisation problem experienced with such implants has been recognised in the prior art, as witnessed by my earlier U.S. Pat. No. 4,315,337.

The invention will now be described, by way of example with reference to the accompanying drawings, in which.

Figure 1:
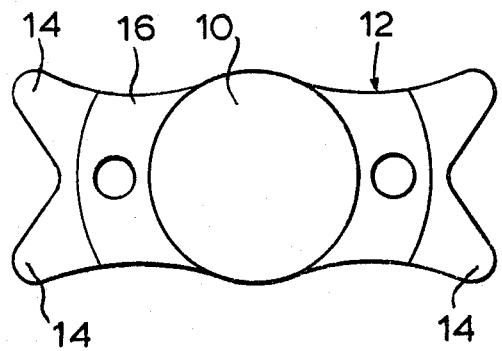
FIG. 1 is a plan view of a Mk IX implant.
Figure 2:
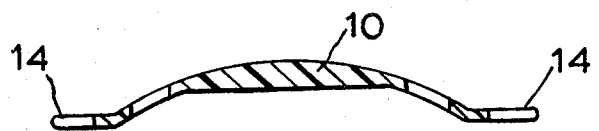
FIG. 2 is a section through the mid-plane of the implant shown in FIG. 1.

The implant in the drawings is generally similar in appearance to a conventional Mk IX implant made from PMMA as described in my U.S. Pat. No. 4,277,851, though the lens is thinner for any given power. The implant comprises an optic 10 and a haptic 12, the latter consisting of feet 14 connected to the optic 10 by part frusto-conical portions 16. The haptic is waisted and fenestrated in order to minimize the obstruction to the circulation of aqueous humor. Because the construction of the implant is already described in detail in the above patent, it is believed that no further description is required within the present context.

The essential difference in the implant in accordance with the invention resides in the choice of material and in the method employed for sterilisation. The preferred material is a polysulphone available from the Union Carbide Corporation under the trade name Udel. This is a substantially clear plastics material having the composition:

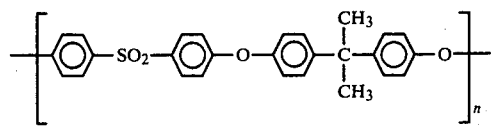

where n is between 10 and 500.

The refractive index of the material is 1.633 relative to aqueous humour, this being significantly higher than conventionally used plastics materials, such as PMMA. This material is also capable of withstanding substantial temperatures without its optical properties being deteriorated.

In order to sterilise an implant after it has been manufactured, the implant is placed carefully in a glass vial containing approximately 3 ml of 0.9% w/v saline solution. Each vial is stoppered and sealed using a crimped aluminum collar. The implant is then autoclaved in the sealed vial for 40 minutes at 116° C.

In batch processing of implants, each autoclave batch additionally contains a spore strip packed in an identical vial to the implant which is analysed after autoclaving. Following autoclaving, each vial in a batch is inspected for integrity of seal and for unwanted inclusions before being dispatched.

It will be appreciated that while the invention has been described by reference to the Choyce Mark IX implant, the same material and sterilisation methods may be employed for other forms of implants, in particular posterior chamber implants.

I claim:

1. An intra-ocular lens which is formed entirely of a polysulfone plastics material which is capable of being worked to produce a lens of optical quality, which has a specific gravity in excess of 1.55 and which is capable of being autoclaved in steam at a temperature in excess of 110° C.

2. An intra-ocular lens as set forth in claim 1, wherein the polysulfone material is an aromatic polysulfone containing repeating units having the formula:

where Ar is a divalent aromatic radical containing at least one unit having the structure:

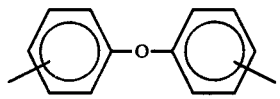

3. An intra-ocular lens as set forth in claim 2, wherein the polysulphone material is composed of repeating units of the structure:

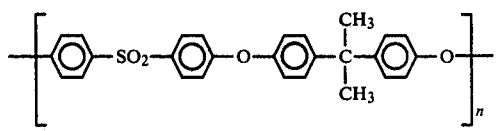

where n = 10 to 500.

* * * * *